United States Patent [19]

Baker

[11] Patent Number: 4,802,912

[45] Date of Patent: Feb. 7, 1989

[54] HERBICIDE ANTIDOTES

[75] Inventor: Don R. Baker, Orinda, Calif.

[73] Assignee: Stauffer Chemical Co., Westport, Conn.

[21] Appl. No.: 566,009

[22] Filed: Dec. 27, 1983

Related U.S. Application Data

[63] Continuation-in-part of Ser. No. 291,207, Aug. 10, 1981, abandoned.

[51] Int. Cl.$^4$ .............................................. A01N 2/32
[52] U.S. Cl. ........................................ 71/100; 71/103; 568/21; 568/27
[58] Field of Search ..................... 71/100, 103, 98; 260/607 R, 607 A, 608; 568/27, 21

[56] References Cited

U.S. PATENT DOCUMENTS

| | | | |
|---|---|---|---|
| 4,009,190 | 2/1977 | Baker | 260/456 R |
| 4,009,191 | 2/1977 | Baker | 260/456 R |
| 4,021,224 | 5/1977 | Pallos et al. | 71/88 |
| 4,021,229 | 5/1977 | Arneklev et al. | 71/100 |
| 4,098,599 | 7/1978 | Arneklev | 71/100 |
| 4,115,099 | 9/1978 | Arneklev | 71/93 |
| 4,230,874 | 10/1980 | Pallos et al. | 560/12 |
| 4,293,701 | 10/1981 | Pallos et al. | 546/335 |
| 4,294,772 | 10/1981 | Martin | 260/429.7 |
| 4,341,901 | 7/1982 | Ruffing et al. | 564/99 |
| 4,358,308 | 11/1982 | Swithenbank | 71/98 |

*Primary Examiner*—Catherine L. Mills
*Attorney, Agent, or Firm*—Harry A. Pacini; Leona L. Lauder

[57] ABSTRACT

This invention relates to haloalkyl-sulfenoxyl-2, 3-dibromopropane compounds and their use as antidotes for thiocarbamate herbicides.

10 Claims, No Drawings

HERBICIDE ANTIDOTES

CROSS REFERENCE TO RELATED APPLICATIONS

This application is a continuation-in-part application of application Ser. No. 291,207, filed Aug. 10, 1981, now abandoned.

FIELD OF THE INVENTION

This invention relates to herbicide antidotes, and, more particularly to mono- or poly-haloalkyl-sulfenoxyl-2,3-dibromopropane antidotes for thiocarbamate herbicides.

BACKGROUND OF THE INVENTION

An herbicide is a compound which adversely controls or modifies plant growth, e.g., killing, retarding, defoliating, desiccating, regulating, stunting, tillering, stimulating, and dwarfing. The term "plant" refers to all physical parts of a plant, including seeds, seedlings, saplings, roots, tubers, stems, stalks, foliage, and fruits. "Plant growth" includes all phases of development from seed germination to natural or induced cessation of life.

Herbicides are generally used to control or eradicate weed pests. They have gained a high degree of commercial success because it has been shown that such control can increase crop yield and reduce harvesting costs.

The most popular methods of herbicide application include: preplant incorporation into the soil; in-furrow application to seeds and surrounding soil; pre-emergence surface treatment of seeded soil; and post-emergence treatment of the plant and soil.

A manufacturer of an herbicide generally recommends a range of application rates and concentrations calculated to maximize weed control. The range of rates varies from approximately 0.01 to 50 pounds per acre (0.0112 to 56 kilograms per hectare (k/ha)), and is usually in the range of from 0.1 to 25 pounds per acre (0.112 to 28 k/ha). The term "herbicidally effective amount" describes the amount of an herbicide compound which adversely controls or modifies plant growth. The actual amount used depends upon several considerations, including particular weed susceptibility and overall cost limitations.

The most important factor influencing the usefulness of a given herbicide is its selectivity towards crops. In some cases, a beneficial crop is susceptible to the effects of the herbicide. In addition, certain herbicidal compounds are phytotoxic to some weed species but not to others. To be effective, an herbicide must cause minimal damage (preferably no damage) to the beneficial crop while maximizing damage to weed species which plague that crop.

To preserve the beneficial aspects of herbicide use and to minimize crop damage, many herbicide antidotes have been prepared. These antidotes reduce or eliminate damage to the crop without substantially impairing the damaging effect of the herbicide on weed species; See, for example, U.S. Pat. Nos. 4,021,224 and 4,021,229 and Belgian Pat. No. 846,894.

The precise mechanism by which an antidote reduces herbicidal crop injury has not been established. An antidote compound may be a remedy, interferent, protectant, or antagonist. As used herein, "antidote" describes a compound which has the effect of establishing herbicide selectivity, i.e., continued herbicidal phytotoxicity to weed species and reduced or non-phytotoxicity to cultivated crop species. The term "antidotally effective amount" describes the amount of an antidote compound which counteracts a phytotoxic response of a beneficial crop to an herbicide.

Thiocarbamate herbicides are particularly effective in the control of grassy type weeds which interfere with the cultivation of a wide variety of crops, e.g., barley, corn, cotton, lentils, peanuts, peas, potatoes, soybeans, spinach, tobacco and tomatoes. Frequently the effective use of these herbicides requires the addition of an antidote compound.

DESCRIPTION OF THE INVENTION

It has now been discovered that mono- and poly-haloalkyl sulfenoxyl-2,3-dibromopropane compounds are effective antidotes for the protection of a variety of crops from thiocarbamate herbicide injury. These antidote compounds have the following formula:

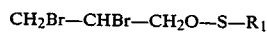

$$CH_2Br-CHBr-CH_2O-S-R_1$$

wherein $R_1$ is a mono or poly-haloalkyl group having 1 to 4 carbon atoms, inclusive.

$R_1$ can be, for example, mono-, di-, or tri-halomethyl, wherein halo is preferably chlorine, bromine or fluorine, and similarly substituted ethyl, propyl and butyl groups. $R_1$ is preferably a polyhaloalkyl and more preferably a polychlorinated methyl or ethyl group. A preferable representative antidote of the instant invention is 1-trichloromethane sulfenoxyl-2,3-dibromopropane having the formula

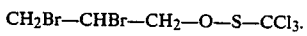

$$CH_2Br-CHBr-CH_2-O-S-CCl_3.$$

This invention also embodies a two-part herbicidal system comprised of:

(a) an herbicidally effective amount of a thiocarbamate compound of the formula:

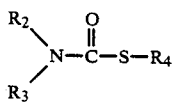

in which $R_2$ is alkyl having 1-6 carbon atoms, inclusive;

$R_3$ is selected from the group consisting of alkyl having 1-6 carbon atoms, inclusive; and cyclohexyl; or $R_2$ and $R_3$ form indistinguishable parts of a single alkylene ring having 4–10 carbon atoms, inclusive; and $R_4$ is selected from the group consisting of alkyl having 1-6 carbon atoms, inclusive; haloalkyl wherein halo is selected from the group consisting of chlorine, bromine and iodine and alkyl has 1-6 carbon atoms, inclusive; alkenyl having 2-6 carbon atoms, inclusive; haloalkenyl wherein halo is selected from the group consisting of chlorine, bromine and iodine and alkenyl has 2-6 carbon atoms, inclusive; benzyl; and halo-substituted benzyl, wherein halo is selected from the group consisting of chlorine, bromine and iodine; and (b) a non-phytotoxic antidotally effective amount of a compound of the formula

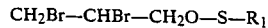

$$CH_2Br-CHBr-CH_2O-S-R_1$$

wherein $R_1$ is a mono- or poly-haloalkyl group having 1 to 4 carbon atoms, inclusive.

By way of exemplification, the active thiocarbamate herbicides employed in the invention may include: S-ethyl N,N-dipropyl thiocarbamate, S-ethyl N,N-diisobutyl thiocarbamate, S-propyl N,N-dipropyl thiocarbamate, S-propyl-N-butyl-N-ethylthiocarbamate, S-(2,3,3-tri-chloroallyl)diisopropyl thiocarbamate, S-ethyl N-ethyl N-cyclohexyl thiocarbamate, S-ethyl hexahydro- 1H-azepine-1-carbothioate, isopropyl hexahydro-1,4-azepine-1-carbothioate, S-benzyl N,N-di-sec-butylthiocarbamate, S-(4-chlorobenzyl) N,N-diethyl thiocarbamate and combinations thereof.

This invention also includes the method of controlling undesirable vegetation and reducing herbicidal crop injury due to a thiocarbamate herbicide which comprises applying to the locus where protection is desired an antidotally effective amount of a compound of the formula $$CH_2Br-CHBr-CH_2-O-S-R_1$$

wherein $R_1$ is mono- or poly-haloalkyl having 1 to 4 carbon atoms, inclusive.

Preparation

The thiocarbamates of the present composition are either commercially available or can be prepared by the procedures described in U.S. Pat. Nos. 2,913,327; 2,983,747; 3,133,947; 3,185,720; and 3,198,786.

The following is a representative preparation for the instant mono- or poly-haloalkyl sulfenoxyl-2,3-dibromopropane antidote compounds.

EXAMPLE 1

Preparation of 1-Trichloromethane sulfenoxyl-2,3-dibromopropane

Ten and two-tenths milliliters (ml) (0.10 mole) of 2,3-dibromo-1-propanol, 11 ml (0.10 mole) of perchloromethyl mercaptan, and 100 ml of ether were combined in a reaction flask. Fifteen and two-tenths ml of triethylamine in 80 ml of ether were added over a period of 2½ hours at 8°-18° C. with stirring and cooling. The mixture was stirred for 2 hours, washed twice with water, dried over magnesium sulfate and evaporated in vacuo to yield 18 g of 1-trichloromethanesulfenoxyl-2,3-dibromopropane, a yellow oil. $n_D^{30} = 1.4922$

Testing

Stock solutions of the herbicides were prepared by diluting the requisite amount of each herbicide in water. Examples of solution compositions and application rates are summarized in Table II.

TABLE I

| Herbicide Stock Solutions | | | | |
|---|---|---|---|---|
| | Composition | | Application | |
| Herbicide Name | Herbicide (mg)* | Water (ml) | ml/flat** | lb/acre |
| EPTAM ® 6E S—ethyl-N,N—dipropyl thiocarbamate | 56 672 | 100 100 | 5 5 | 0.50 6.00 |

*The weight is measured in terms of mg of formulated herbicide. The formulation used contained about 72% active herbicide compound.
**The flats measure 5.95 inches by 9.5 inches. Approximately four (4) mg/flat is equal to one (1) lb/acre.

In all cases, the herbicide was incorporated into the soil prior to planting.

Stock solutions of the antidote compounds were prepared at the desired concentrations by diluting the requisite amounts of each antidote in acetone. An example of a solution composition, rate and application method is summarized in Table II.

TABLE II

| Antidote Stock Solutions | | | | |
|---|---|---|---|---|
| Antidote: 1-Trichloromethanesulfenoxyl-2,3-dibromopropane | | | | |
| Composition | | Application | | |
| Antidote (mg) | Acetone (ml) | ml/flat | lb/acre | Method |
| 100 | 25 | 5.00 | 5.00 | PPI* |

*PPI = Pre-plant incorporation of antidote.

The antidote was also incorporated into the soil prior to planting in all cases.

Control flats contained crops treated with herbicide only. All flats were placed on greenhouse benches where temperature was maintained between 70° and 90° F. (21.1° to 32.2° C.). The flats were watered by sprinkling as needed to assure good plant growth.

The treated crops initially screened for herbicidal injury were milo, wheat, cotton, rice, barley, corn, soybeans and sugarbeets. The compound was tested on the following weed species:

| Common Name | Abbreviation | Scientific Name |
|---|---|---|
| foxtail | FT | (Setaria viridis) |
| red oat | RO | (Avena sativa) |
| mustard | MD | (Brassica juncea) |
| lambsquarter | LQ | (Chenopodium spp.) |

Herbicide

EPTAM ® = S-ethyl-N,N-dipropyl thiocarbamate

Application Method

PPI = Pre-plant incorporation of herbicide or antidote.

If no antidote was applied, the word "none" appears in the Antidote Rate column. These are the control flats for each crop. The results shown on this line are the percent injuries sustained by each of the crops when treated with the herbicide only at the rate specified.

All rates shown, for both herbicide and antidote, are in pounds per acre.

Injury Ratings

The injury to the crop (Table III) or weeds (Table IV) is shown as a percentage of damage done to the plants as compared to an evaluation of the overall undamaged state of the plants. The damage done to the plants is a function of the number of plants injured and the extent of injury to each plant. This rating is made four (4) weeks after application of the herbicide alone or of the herbicide in combination with the antidote.

An asterisk (*) in Table III indicates that the representative antidote compound is active in reducing herbicidal injury to the crop.

Table IV shows that the representative antidote compound has no effect on weeds, i.e., herbicidal injury to the weeds is sustained even in the presence of the antidote compound.

TABLE III

| Cmpd. No. | Herbicide Name | Rate | Antidote Rate | Method | Milo % Inj | Wheat % Inj | Cotton % Inj | Rice % Inj | Barley % Inj | Corn % Inj | Soybean % Inj | Sugar Beets % Inj |
|---|---|---|---|---|---|---|---|---|---|---|---|---|
| 1 | EPTAM | 0.50 | none | — | 60 | 90 |  | 80 | 70 |  |  |  |
|  | EPTAM | 0.50 | 5.00 | PPI | *40 | 95 |  | 80 | *60 |  |  |  |
|  | EPTAM | 3.00 | none | — |  |  | 70 |  |  | 60 | 60 | 40 |
|  | EPTAM | 3.00 | 5.00 | PPI |  |  | 70 |  |  | *0 | *40 | *20 |
|  | EPTAM | 6.00 | none | — |  |  |  |  |  |  |  | 70 |
|  | EPTAM | 6.00 | 5.00 | PPI |  |  |  |  |  |  |  | 70 |
|  | EPTAM | 6.00 | 10.0 | PPI |  |  |  |  |  |  |  | 70 |

TABLE IV

| Herbicide Name | Rate | Antidote Rate | Method | FT | RO | MD | LQ |
|---|---|---|---|---|---|---|---|
| EPTAM | 0.50 | none | — | 50 | 95 |  |  |
| EPTAM | 0.50 | 5.00 | PPI | 50 | 93 |  |  |
| EPTAM | 3.00 | none | — |  |  | 10 |  |
| EPTAM | 3.00 | 5.00 | PPI |  |  | 0 |  |
| EPTAM | 6.00 | none | — |  |  | 70 | 70 |
| EPTAM | 6.00 | 5.00 | PPI |  |  | 60 | 70 |
| EPTAM | 6.00 | 10.0 | PPI |  |  | 60 | 70 |

Test Results

A representative antidote compound of the instant invention, 1-trichloromethanesulfenoxyl-2,3-dibromopropane, shows good antidotal activity for a variety of crops. Use of this compound did not result in a reduction of herbicidal injury to weeds.

Formulations

A formulation is the incorporation of a formulant in a form which is directly usable on crops and weeds. As defined herein, a "formulant" is the material which is to be formulated. The formulant may be either an antidote compound alone or an herbicide and antidote composition. The purpose of the formulation is to apply the formulant to the locus where it is desired to establish herbicidal selectivity by a convenient method. The "locus" may include soil, seeds, seedlings and vegetation.

The formulatons are commonly dusts, wettable powders, granules, solutions or emulsifiable concentrates.

Dusts are free-flowing powder compositions containing the formulant impregnated on a particulate carrier. The particle size of the carriers is usually in the approximate range of 30 to 50 microns. Examples of suitable carriers are talc, bentonite, diatomaceous earth, and pyrophyllite. The composition generally contains up to 50% of formulant. Anti-caking and anti-static agents may also be added. Dusts may be applies by spraying from boom and hand sprayers on airplanes.

Wettable powders are finely divided compositions comprising a particulate carrier impregnated with the formulant and additionally containing one or more surface active agents. The surface active agent promotes rapid dispersion of the powder in an aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhdyric alcohols, in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the formulant impregnated on a particulate inert carrier having a particle size of about 1 to 2 millimeters (mm) in diameter. The granules can be made by spraying a solution of the formulant in a volatile solvent onto the granular carrier. Examples of suitable carriers for the preparation of granules include clay, vermiculite, sawdust, and granular carbon.

Emulsifiable concentrates consist of an oil solution of the formulant plus an emulsifying agent. Prior to use the concentrate is diluted with water to form a suspended emulsion of oil droplets. The emulsifiers used are usually a mixture of anionic and nonionic surfactants. Other additives, such as suspending agents and thickeners, may be included in the emulsifiable concentrate.

When the formulant is an antidote and herbicide composition, the proportion of antidote compound to herbicide compound generally ranges from approximately 0.001 to 30 parts by weight of the antidote compound per weight of the herbicide compound.

Formulations generally contain several additives in addition to the formulant and carrier or agent. Among these are inert ingredients, diluent carriers, organic solvents, water, oil and water, water in oil emulsions, carriers of dusts and granules, and surface active wetting, dispersing and emulsifying agents. Fertilizers, e.g., ammonium nitrate, urea and superphosphate, may be included. Aids to rooting and growth, e.g., compost, manure, humus and sand, may also be included.

Alternatively, the antidote compounds and herbicide and antidote compositions of this invention can be applied to a crop by addition of the formulant to irrigation water supplied to the field to be treated. This method of application permits the penetration of the compositions into the soil as the water is absorbed.

As another alternative, the formulant can be applied to the soil in the form of a solution in a suitable solvent. Solvents frequently used in these formulations include kerosene, fuel oil, xylene, petroleum fractions with boiling ranges above xylene and aromatic petroleum fractions rich in methylated naphthalenes. Liquid solutions, like dusts, may be applied by spraying from boom and hand sprayers on airplanes.

What is claimed is:

1. A compound having the formula

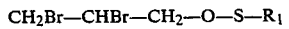

wherein $R_1$ is trihaloalkyl having 1 to 4 carbon atoms, inclusive.

2. A compound according to claim 1 having the formula $CH_2Br-CHBr-CH_2-O-S-CCl_3$.

3. A composition comprising an herbicidally effective amount of a compound as defined in claim 1 with an inert diluent carrier or agent.

4. An herbicidal composition comprising:
(a) an herbicidally effective amount of a thiocarbamate compound of the formula:

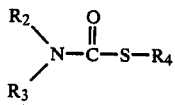

in which
$R_2$ is alkyl having 1-4 carbon atoms, inclusive;
$R_3$ is selected from the group consisting of alkyl having 1-4 carbon atoms, inclusive; and
$R_4$ is selected from the group consisting of alkyl having 1-4 carbon atoms, inclusive; and
(b) a non-phytotoxic antidotally effective amount of a compound of the formula $CH_2Br-CHBr-CH_2-O-S-R_1$ wherein $R_1$ is trihaloalkyl having 1 to 4 carbon atoms, inclusive.

5. An herbicidal composition according to claim 4 wherein $R_1$ is trichloromethyl.

6. A method of controlling undesirable vegetation and reducing herbicidal crop injury caused by an alkyl thiocarbamate herbicide which comprises applying to the locus were control is desired a compound having the formula $CH_2Br-CHBr-CH_2-O-S-R_1$ wherein $R_1$ is a trihaloalkyl having 1 to 4 carbon atoms, inclusive.

7. A method according to claim 6 wherein $R_1$ is trichloromethyl.

8. A method of controlling undesirable vegetation and reducing herbicidal crop injury caused by an alkyl thiocarbamate herbicide which comprises applying to the locus where control is desired a composition comprising
(a) an herbicidally effective amount of a thiocarbamate compound of the formula:

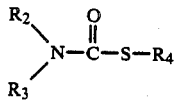

in which
$R_2$ is alkyl having 1-4 carbon atoms, inclusive;
$R_3$ is selected from the group consisting of alkyl having 1-4 carbon atoms, inclusive; and
$R_4$ is selected from the group consisting of alkyl having 1-4 carbon atoms, inclusive; and
(b) a non-phytotoxic antidotally effective amount of a compound of the formula $CH_2Br-CHBr-CH_2O-S-R_1$ wherein $R_1$ is trihaloalkyl having 1 to 4 carbon atoms, inclusive.

9. A method as defined in claim 7 wherein $R_1$ is trichloromethyl.

10. A method as defined in claim 8 wherein $R_2$ and $R_3$ are both propyl and $R_4$ is ethyl.

* * * * *